US00PP15844P2

(12) United States Plant Patent
Warren et al.

(10) Patent No.: US PP15,844 P2
(45) Date of Patent: Jul. 5, 2005

(54) ***CALLA* LILY PLANT NAMED 'JACK OF HEARTS'**

(50) Latin Name: *Zantedeschia spp.*
Varietal Denomination: Jack of Hearts

(75) Inventors: Andrew Geoffrey Fiennes Warren, Tauranga (NZ); Jacobus Petrus Spaans, Tauranga (NZ)

(73) Assignee: Bloomz Limited, Tauranga (NZ)

( * ) Notice: Subject to any disclaimer, the term of this patent is extended or adjusted under 35 U.S.C. 154(b) by 33 days.

(21) Appl. No.: 10/766,114

(22) Filed: Jan. 27, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Jondle & Associates P.C.

(57) ABSTRACT

A *calla* lily plant particularly distinguished by red spathe and maculated leaves.

3 Drawing Sheets

Genus and species: *Zantedeschia spp.*
Variety denomination: 'Jack of Hearts'.

BACKGROUND OF THE NEW PLANT

The present invention comprises a new and distinct cultivar of *calla* lily, botanically known as *Zantedeschia* spp, and hereinafter referred to by the cultivar name 'Jack of Hearts'. The new cultivar is asexually reproduced from vegetative cuttings and tissue culture resulting from the cross of the female parent 'Sunglow' (patent status unknown) and the male parent, an unknown seedling from the Bloomz breeding pool (not patented).

'Jack of Hearts' is a product of a planned breeding program intended to create new *calla* lily plants with red spathes.

The new cultivar was created in 2000 in Tauranga New Zealand and has been asexually reproduced repeatedly by vegetative cuttings and tissue culture in Tauranga, New Zealand and Bangalore, India over a 2 year period. The present invention has been found to retain its distinctive characteristics through successive propagations; and this novelty is firmly fixed.

DESCRIPTION OF PHOTOGRAPH

This new *calla* lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
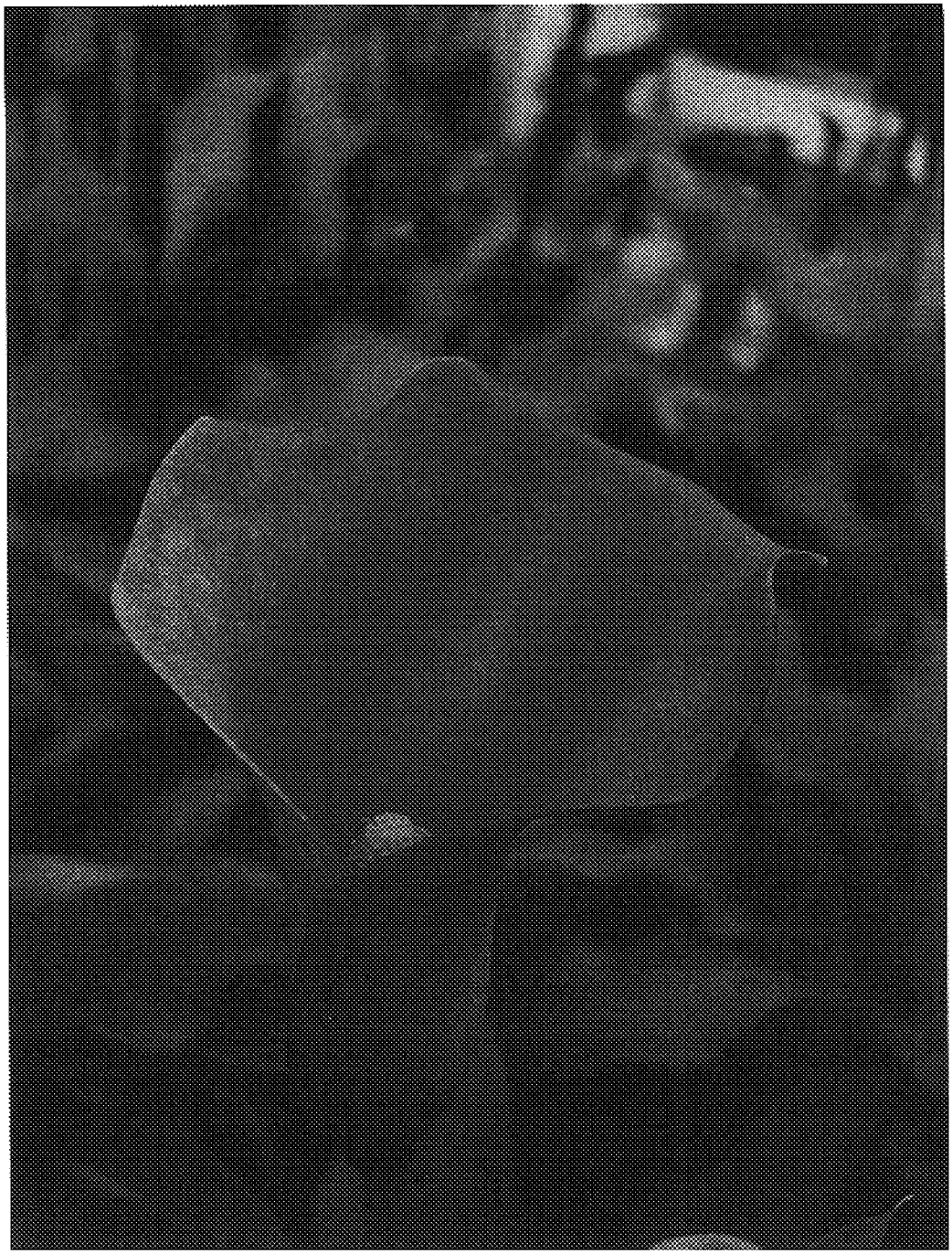
FIG. 1 shows the mature inflorescence.
Figure 2:
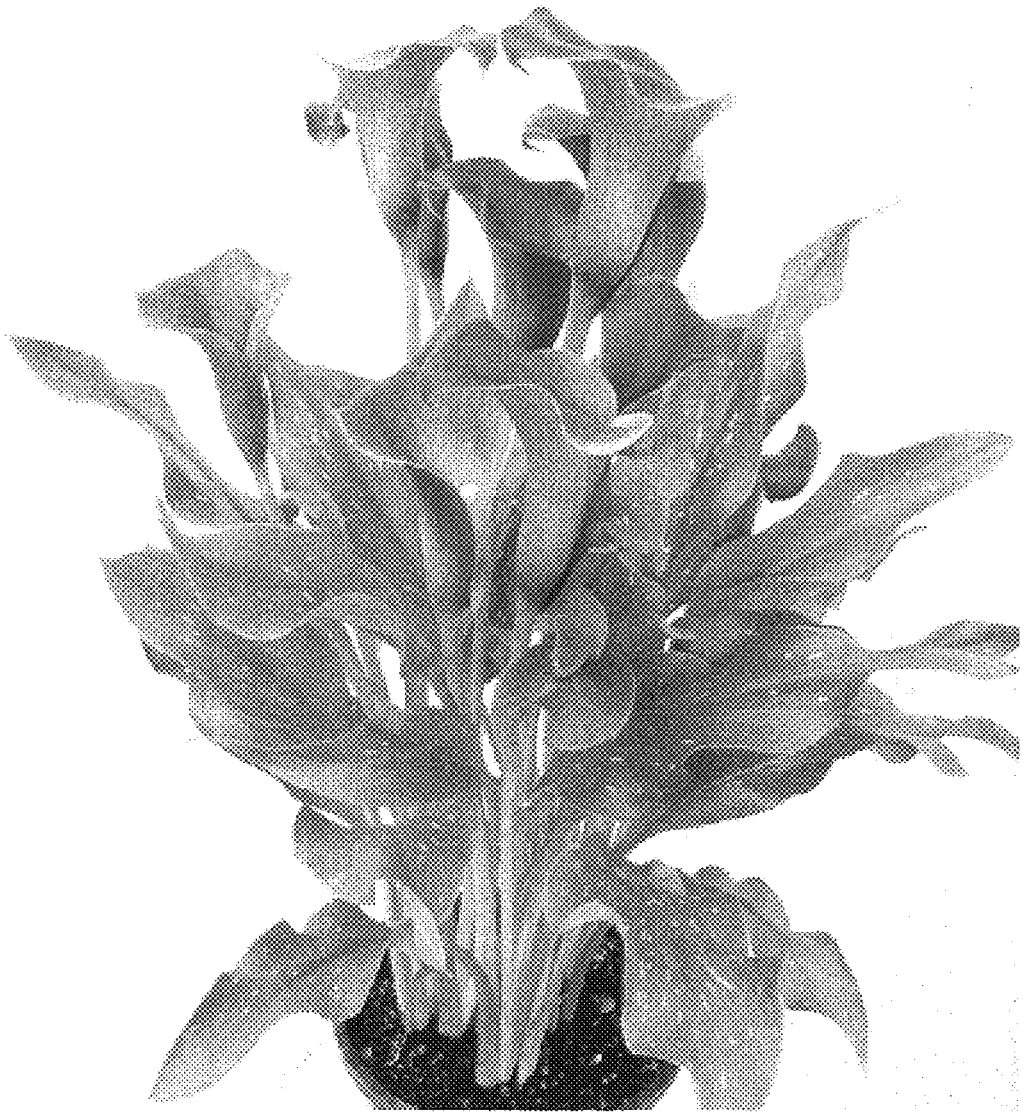
FIG. 2 shows the overall plant habit.
Figure 3:
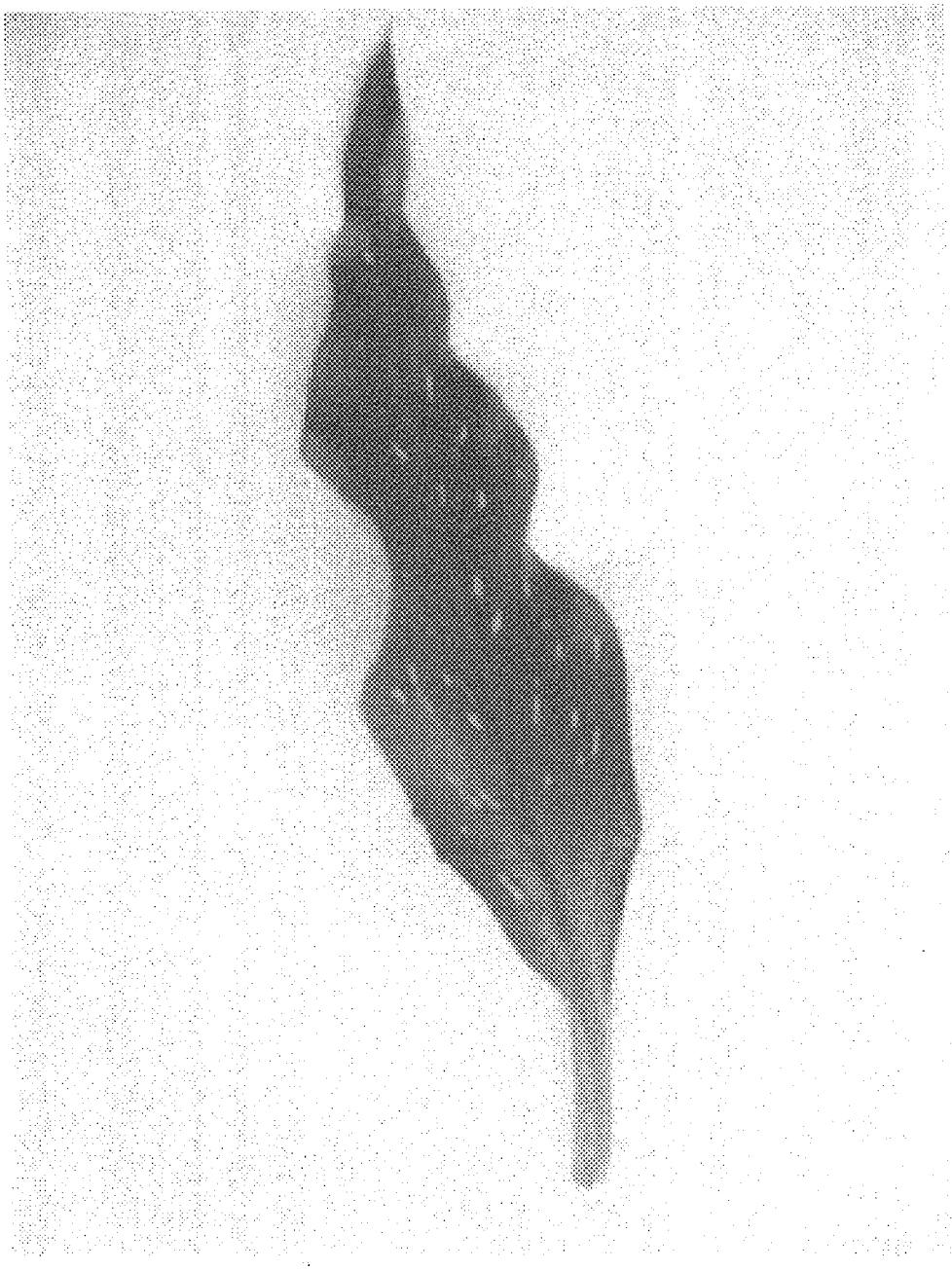
FIG. 3 shows a close-up of the leaf.

The following detailed descriptions set forth the distinctive characteristics of 'Jack of Hearts'. The data that defines these characteristics were collected from asexual reproductions carried out in New Zealand. The plant history was taken on 2 year old plants based on a 4 cm diameter tuber under New Zealand Summer conditions. Color references are primarily to The R.H.S. Colour Chart of The Royal Horticultural Society of London (R.H.S.).

THE PLANT

Classification:
- *Botanical.*—*Zantedeschia* spp.
- *Commercial.*—*Calla* lily.
- *Variety.*—'Jack of Hearts'.

Size:
- *Form.*—Erect.
- *Height of the leaf canopy above the soil.*—25–30 cm.
- *Height of top of inflorescence above the soil.*—25–35 cm.
- *Diameter.*—20–30 cm.
- *Number of inflorescence per tuber size.*—Tuber diameter 3 cm: 2–3. Tuber diameter 4 cm: 3–6. Tuber diameter 5 cm: 5–8.

Branches:
- *Character.*—Strong.
- *Color.*—Upper is green RHS 146C; lower is green RHS 146D; base is white RHS 155B.
- *Average number.*—3–5.

Leaves:
- *Size.*—Width 4–16 cm; length 14–20 cm.
- *Shape.*—Ovate.
- *Color.*—Upper is green RHS 137C; lower is green RHS 137B.
- *Maculation* (*leaf spots*).—Medium density; white RHS 155C.
- *Apex.*—Acute to apiculate.
- *Margin.*—Moderately wavy.
- *Margin color.*—Yellow-Green RHS 137B.
- *Veins.*—Pinnate.
- *Surface quality.*—Leathery.

Petiole (leaf stalk):
- *Length.*—10–15 cm.
- *Color.*—Base is Green RHS 146D; upper is green RHS 146C.

Roots:
- *Color.*—White.
- *Branching.*—Not branched, attached to the top of the tuber at the apices.
- *Disease resistance.*—No susceptibility noted to date.
- *Pest resistance.*—No susceptibility noted to date.

THE INFLORESCENCE

Spathe (flower body):
- *Size.*—Length 6–8 cm; width 4–5 cm.

*Color.*—Upper is Dark red RHS 60B; lower is dark red RHS 60C.
*Veins.*—Present, dark red RHS 60A.
*Shape.*—Cupped.

Spadix (reproductive organs):
*Size.*—Length 2–3 cm; diameter 0.5–0.8 cm.
*Color.*—Base is green RHS 146D; Upper is dark red RHS 60C.
*Position relative to spath.*—Upright.

Peduncle (flower stem):
*Size.*—25–35 cm.
*Color.*—Base is White RHS 155B; upper is green RHS 146B.

Reproductive organs:
*Location of female organs.*—Basal position of the spadix.
*Location of male organs.*—Upper position of the spadix.
*Perianth* (*the floral envelope — calyx and corolla*).—Conspicuous.
*Stamens.*—Not visible before pollen release.
*Pistil.*—18–25 per spadix; red-green.

Miscellaneous:
*Time to produce a finished flowering plant.*—6–8 weeks.
*Lastingness.*—1–3 weeks.
*Fragrance.*—None.
*Fruit.*—None.
*Production.*—18–25 berries.
*Color.*—Predominantly green RHS 146A.

COMPARISON WITH KNOWN CULTIVARS

When the instant plant is compared to 'Pink Pot' (co-pending U.S. patent application Ser. No. 10/382,759) 'Jack of Hearts' has a coarser maculation on the leaves and a flower color that is more pink red instead of bright pink. 'Sunglow,' the female parent, has a yellow to orange spathe and medium green ovate foliage with light maculation while 'Jack of Hearts' has a pink red spathe and the foliage has medium maculation. The male parent has a red-purple spathe and light maculation of the foliage while 'Jack of Hearts' has a pink red spathe and the foliage has medium maculation.

I claim:

1. A new and distinct cultivar of *calla* lily plant as shown and described herein.

* * * * *